United States Patent [19]

Yoshioka et al.

[11] Patent Number: 4,778,883
[45] Date of Patent: Oct. 18, 1988

[54] 3-(CHFCH₃)-AZETIDINONE INTERMEDIATES

[75] Inventors: Takeo Yoshioka, Ayase; Noritaka Chida, Sagamihara; Azuma Watanabe, Yokohama; Yasuo Fukagawa, Kamakura; Tomoyuki Ishikura, Chigasaki, all of Japan

[73] Assignee: Sanraku Incorporated, Tokyo, Japan

[21] Appl. No.: 16,106

[22] Filed: Feb. 18, 1987

[30] Foreign Application Priority Data

Feb. 19, 1986 [JP] Japan .................................. 61-32717
Jul. 7, 1986 [JP] Japan ................................ 61-157889

[51] Int. Cl.⁴ ................. C07D 205/08; C07D 405/04; C07F 7/10; C07B 39/00
[52] U.S. Cl. .................................... 540/200; 540/357
[58] Field of Search ............................... 540/357, 200

[56] References Cited

PUBLICATIONS

Mak I, Chem. Abs. 101, 23217u (1984).
Mak II, Chem. Ab. 103, 19594j (1985).

*Primary Examiner*—Mark L. Berch
*Attorney, Agent, or Firm*—Wenderoth, Lind & Ponack

[57] ABSTRACT

An azetidinone derivative of the formula

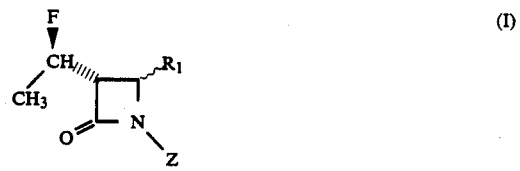
(I)

wherein $R_1$ represents a formyl group, a carboxyl group, an acetyloxy group or a group of the formula

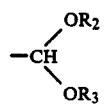

in which $R_2$ and $R_3$ each represent a lower alkyl group or together represent a lower alkylene group, and Z represents a hydrogen atom or an amino-protecting group.

5 Claims, No Drawings

3-(CHFCH₃)-AZETIDINONE INTERMEDIATES

This invention relates to novel azetidinone derivatives, and more specifically, to azetidinone derivatives of the following formula

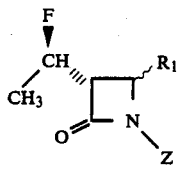

(I)

wherein R₁ represents a formyl group, a carboxyl group, an acetyloxy group or a group of the formula

in which R₂ and R₃ each represent a lower alkyl group or together represent a lower alkylene group, and Z represents a hydrogen atom or an amino-protecting group.

The compounds of formula (I) provided by this invention are useful as intermediates for synthesis of various pharmaceuticals, particularly carbapenam or carbapenem antibiotics, for example an antibiotic of the following formula

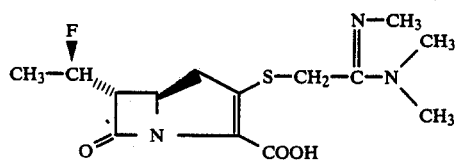

(A)

which is known to be a relatively stable carbapenem antibiotic having excellent antimicrobial activity.

The antibiotic of formula (A) and a method of its production were first developed by Sandoz AG of Switzerland and are disclosed in United Kingdom Pat. No. 2124625. The method of producing the antibiotic of formula (A) disclosed there requires quite a number of steps and complex reaction operations and is not believed to be industrially suitable.

The present inventors therefore made extensive investigations on a relatively simple method of producing the antibiotic of formula (A) which comprises a smaller number of steps. These investigations have now led to the discovery that by using the novel azetidinone derivatives of formula (I) above as intermediates, the antibiotic of formula (A) can be obtained in good yields through a relatively few steps.

The term "lower", as used herein to qualify a group or a compound, means that the group or compound so qualified has not more than 6, preferably not more than 4, carbon atoms.

The "lower alkyl group" may be linear or branched, and includes, for example methyl, ethyl, n-propyl, isopropyl, n-butyl, sec-butyl, isobutyl, tert-butyl, n-pentyl and n-hexyl groups. The "lower alkylene group" may have a branched chain, and includes, for example, ethylene, trimethylene, tetramethylene, methylethylene, 1,2-dimethylethylene, 1-methyltrimethylene, 2-methyl-trimethylene, 1,3-dimethyltrimethylene, ethylethylene, 1,2-diethylethylene, 1,1,3,3-tetramethyltriethylene and 2,2-dimethyltrimethylene. The "amino-protecting group" includes, for example, tri-(lower alkyl)-silyl groups such as trimethylsilyl and tert-butyldimethylsilyl, aralkyl groups such as benzyl and substituted or unsubstituted phenyl groups such as p-methoxyphenyl and p,p-dimethoxyphenyl.

In formula (I), the configuration of the substituent R₁ at the 4-position may be S or R.

Typical examples of the compounds of formula (I) provided by this invention are given below.

(3R,4R)- or (3R,4S)-3-[(R)-fluoroethyl]-4-formyl-1-(p-methoxy)phenyl-2-azetidinone, (3R,4R)- or (3R,4S)-1-benzyl-3-[(R)-1-fluoroethyl]-4-formyl-2-azetidinone, (3R,4R)- or (3R,4S)-3-[(R)-1-fluoroethyl)-4-formyl-1-trimethylsilyl-2-azetidinone, (3R,4R)- or (3R,4S)-4-carboxy-3-[(R)-1-fluoroethyl)-1-(p-methoxy)phenyl-2-azetidinone, (3R,4R)- or (3R,4S)-4-carboxy-3-[(R)-1-fluoroethyl]-1-benzyl-2-azetidinone, (3R,4R)- or (3R,4S)-4-carboxy-3-[(R)-1-fluoroethyl]-1-trimethylsilyl-2-azetidinone, (3R,4R)- or (3R,4S)-acetoxy-3-[(R)-1-fluoroethyl]-1-(p-methoxy)phenyl-2-azetidinone, (3R,4R)- or (3R,4S)-4-acetoxy-1-benzyl-3-[(R)-1-fluoroethyl)-2-azetidinone, (3R,4R)- or (3R,4S)-4-acetoxy-3-[(R)-1-fluoroethyl]-1-trimethylsilyl-2-azetidinone, (3R,4R)- or (3R,4S)-4-acetoxy-3-[(R)-1-fluoroethyl]-2-azetidinone, (3R,4R)- or (3R,4S)-4-(dimethoxy)methyl-3-[(R)-1-fluoroethyl]-1-(p-methoxy)phenyl-2-azetidinone, (3R,4R)- or (3R,4S)-1-benzyl-4-(dimethoxy)methyl-3-[(R)-1-fluoroethyl]-2-azetidione, (3R,4R)- or (3R,4S)-4-(dimethoxy)methyl-3-[(R)-1-fluoroethyl]-1-trimethylsilyl-2-azetidinone, (3R,4R)- or (3R,4S)-4-(diethoxy)-methyl-3-[(R)-1-fluoroethyl]-1-(p-methoxy)phenyl-2-azetidinone, (3R,4R)- or (3R,4S)-1-benzyl-4-(diethoxy)methyl-3-[(R)-1-fluoroethyl]-2-azetidinone, (3R,4R)- or (3R,4S)-4-(diethoxy)methyl-3-[(R)-1-fluoroethyl]-1-trimethylsilyl-2-azetidinone, (3R,4R)- or (3R,4S)-4-(ethoxymethoxy)methyl-3-[(R)-1-fluoroethyl]-1-(p-methoxy)phenyl-2-azetidinone, (3R,4R)- or (3R,4S)-1-benzyl-4-(ethoxymethoxy)methyl-3-[(R)-1-fluoroethyl]-2-azetidinone, (3R,4R)- or (3R,4S)-4-(ethoxymethoxy)methyl-3-[(R)-1-fluoroethyl]-1-trimethylsilyl-2-azetidinone, (3R,4R)- or (3R,4S)-4-(1,3-dioxolan-2-yl)-3-[(R)-1-fluoroethyl]-1-(p-methoxy)phenyl-2-azetidinone, (3R,4R)- or (3R,4S)-1-benzyl-4-(1,3-dioxolan-2-yl)-3-[(R)-1-fluoroethyl]-2-azetidinone, and (3R,4R)- or (3R,4S)-4-(1,3-dioxolan-2-yl)-3-[(R)-1-fluoroethyl]-1-trimethylsilyl-2-azetidinone.

The compounds of formula (I) can be produced by the route shown by the following reaction scheme I.

Reaction Scheme I

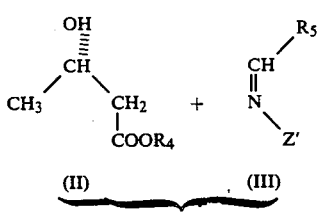

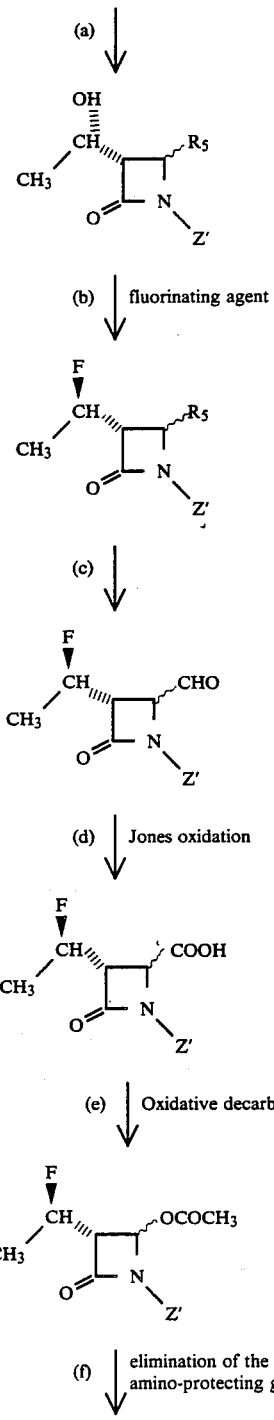

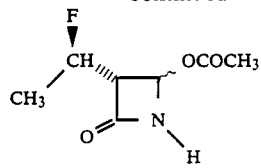

In the above scheme, $R_4$ represents a carboxyl-protecting group, $R_5$ represents a group of the formula

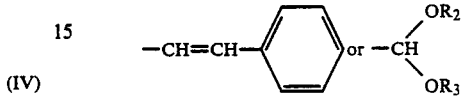

in which $R_2$ and $R_3$ are as defined above, and $Z'$ represents an amino-protecting group.

The compound of formula (II) used as a starting material in step (a) is a compound known per se. Examples of the "carboxyl-protecting group" represented by $R_4$ include lower alkyl groups such as methyl, ethyl, propyl, isopropyl, butyl, sec-butyl and hexyl, aralkyl groups such as benzyl, methoxybenzyl, nitrobenzyl and chlorobenzyl, lower haloalkyl groups such as 2-iodoethyl and 2,2,2-trichloroethyl, lower alkoxymethyl groups such as methoxymethyl and ethoxymethyl, and lower alkanoyloxymethyl groups such as acetoxymethyl, propionyloxymethyl and pivaloyloxymethyl.

The reaction of the compound of formula (II) with the compound of formula (III) can be carried out by a method known per se [for example, see G. I. George et al., J. Chem. Soc. Chem. Commun., 1433 (1985)]. The compound of formula (II) is first converted into its dianion. The structure of the dianion cannot be strictly defined. When an organolithium compound is used as a reagent for dianion formation, the resulting dianion is understood to be of the following formula:

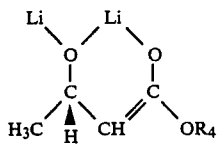

Conversion of the compound of formula (II) into the dianion can usually be carried out by reacting the compound of formula (II) with an organometalic compound having anion-forming ability in a suitable solvent such as a mixture of dimethylformamide and an ether (e.g., diethyl ether, tetrahyrofuran, dimethoxyethane) at a low temperature within the range of $-10°$ to $0°$ C., preferably $-78°$ to $-20°$ C.

Examples of the "organometallic compound having anion-forming ability" that can be preferably used in this reaction are organolithium compounds such as lithium diisopropylamide, lithium isopropylcyclohexylamide, lithium hexamethyldisilazide, tert-butyllithium and methyllithium. Conveniently, the organometallic compound is used in an amount of 1.8 to 2.8 moles, preferably 2.0 to 2.3 moles, per mole of the compound of formula (II).

The dianion so formed is subsequently reacted with the compound of formula (III). The reaction temperature may be generally $-100°$ to $50°$ C., preferably $-78°$ to 25° C. The amount of the compound of formula (III) used is not critical. Generally, it may be 0.8 to 2.0 moles, preferably 0.9 to 1.5 moles, per mole of the compound of formula (II).

The compound of formula (III) used as a starting material in the above reaction can be produced by decomposing cinnamaldehyde or an acetal of acrolein represented by the following formula

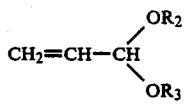

wherein $R_2$ and $R_3$ are as defined hereinabove, with ozone to form a compound of the formula

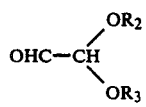

wherein $R_2$ and $R_3$ are as defined above, and reacting the resulting compound with an amine represented by the following formula $NH_2-Z'$ wherein $Z'$ is as defined above.

The above reaction usually gives a mixture of two epimers of the following formulae.

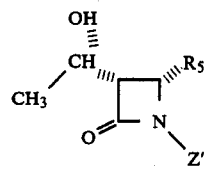

and

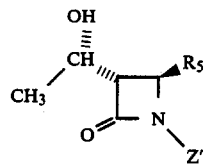

The epimeric mixture may be separated into the constituent epimers at this time, or may be used directly in the subsequent reaction.

The resulting compound of formula (IV) is then treated with a fluorinating agent [step (b)]. Examples of the fluorinating agent are diethylaminosulfur trifluoride (DAST), and hexafluoropropene-diethylaminne (Ishikawa reagent). The reaction of the compound of formula (IV) with the fluorinating agent may be carried out by a method known per se. For example, when DAST is used, the reaction can be carried out by the method described in Ching-Pong Mak et al., Heterocycles, 19, 1399 (1982). When the Ishikawa reagent is used, it can be carried out by the method described in Ishikawa et al., Bull. Chem. Soc. Jpn., 52, 3377 (1979).

As a result, the OH having an S-configuration in the 3-position side chain is stereoselectively replaced in an R-configuration to give the compound of formula (V).

A compound of formula (V) in which $R_5$ represents the group

[to be referred to as the compound of formula (V-a)] can be converted by hydrolysis into a compound of formula (I-a), i.e. a compound of formula (I) in which $R_1$ represents a formyl group.

Hydrolysis of the compound of formula (V-a) may be carried out in a customary manner in the presence of an acid, for example by reacting it with an aqueous solution of hydrochloric acid in an acetic acid-water mixed solvent, or with an aqueous solution of hydrochloric acid or p-toluenesulfonic acid in a tetrahydrofuran-water mixed solvent.

A compound of formula (V) in which $R_5$ represents the group

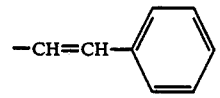

[ to be referred to as the compound of formula (V-b)] is oxidized with ozone to give the compound of formula (I-a). Jones oxidation of this compound yields the compound of formula (I-b), i.e. a compound of formula (I) in which $R_1$ is a carboxyl group [step (d)]. The above ozone oxidation and Jones oxidation can be carried out by methods known per se, for example by the method described in D. J. Hart, Tetrahedron Letters, 26, 5493 (1985).

The resulting compound of formula (I-b) can be converted into a compound of formula (I-c-1), i.e. a compound of formula (I) in which $R_1$ represents an acetyloxy group, by decarboxylating it oxidatively with lead tetraacetate [step (e)]. The oxidative decarboxylation can be carried out by a method known per se, for example by a method substantially in accordance with the method described in P. J. Reider et al., Tetrahedron Letters, 23, 2293 (1982).

The amino-protecting group ($Z'$) of the resulting compound of formula (I-c-1) at the 1-position of the compound of formula (I-c-1) is eliminated by a suitable deprotecting reaction according to the type of the amino-protecting group [for example, by acid hydrolysis when $Z'$ is a tri-(lower alkyl)silyl group, hydrogenolysis when $Z'$ is an aralkyl group, and oxidative elimination when $Z'$ is a p-methoxyphenyl or o,p-dimethoxyphenyl group] to give a compound of formula (I-c-2) [step (f)]. When $Z'$ is a trimethylsilyl group, the resulting compound of formula (I-c-1) may be submitted to the reaction of forming the antibiotic of formula (A) shown in reaction scheme II below without deprotection.

The product in each step of the reaction may, as required, be separated and purified by methods known per se, for example extraction with an organic solvent or silica gel column chromatography.

The compound of formula (I-c-2) so produced can be converted to the antibiotic of formula (A) by a method known per se, for exampled through the steps shown in reaction scheme II below.

Reaction Scheme II

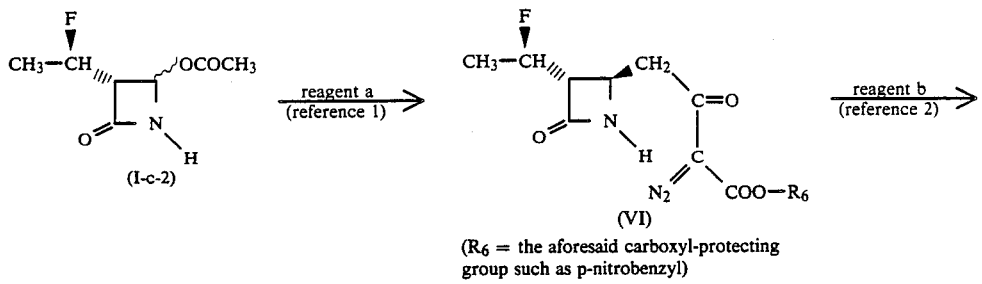

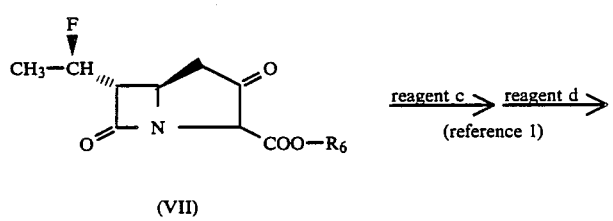

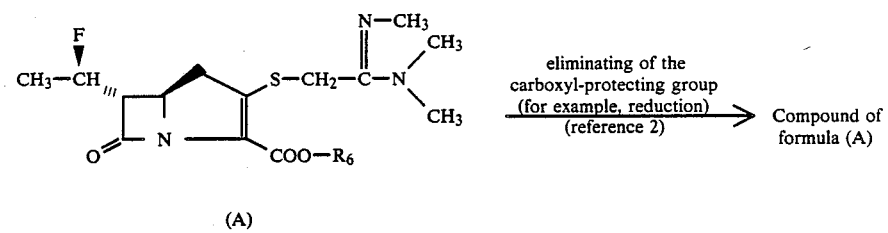

Reagents (a) $H_2C=C[OSi(CH_3)_3]-C(N_2)-COO-R_6$ and $ZnI_2$
(b) $Rh_2(OCOCH_3)_4$
(c)

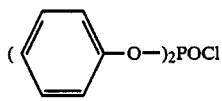

and $(iso-C_3H_7)_2NC_2H_5$, (d)

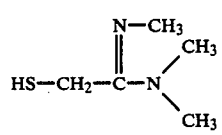

and $(iso-C_3H_7)_2NC_2H_5$

References (1) W. Flitsch et al., Tetrahedron Letters, 23, 2297 (1982).

(2) D. G. Melillo et al., Tetrahedron Letters, 21, 2783 (1980).

The antibiotic of formula (A) produced as above has a wide range of excellent antimicrobial activities and stability to kidney dehydropeptidase, and is very useful as an antimicrobial agent. Accordingly, the compounds of formula (I) provided by this invention are useful as synthetic intermediates for this antibiotic.

The following Examples illustrate the present invention more specifically.

EXAMPLE 1

Production of (3S,4S), (3S,4R) and (3R,4S)-3-[(S)-1-hydroxyethyl]-1-(p-methoxy)phenyl-4-(2-phenyl)vinyl-2-azetidinones Ia, Ib and Ic:

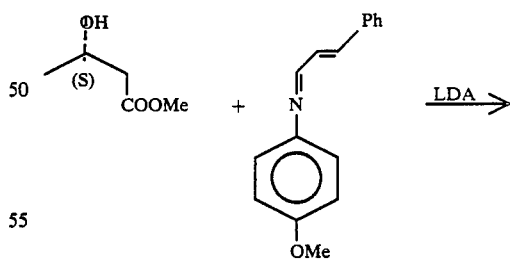

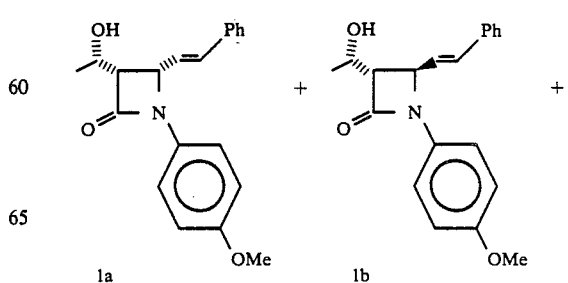

-continued

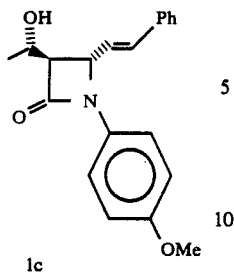

1c

The captioned compounds were synthesized in accordance with the method of G. I. George et al., Journal Chem. Soc. Chem. Commun., 1433 (1985).

A mixture of 15 ml of anhydrous tetrahydrofuran (THF) and 5 ml (35.6 mmoles) of diisopropylamine was cooled to −78° C. and 15 ml (3.9 mmoles) of a 2.6M hexane solution of n-butyllithium was added over the course of 10 minutes, and the mixture was reacted at the same temperature for 15 minutes. To this solution was added dropwise 3 ml of a tetrahydrofuran solution containing 2 g (17 mmoles) of methyl (S)-beta-hydroxybutyrate (optical purity 88%). The mixture was reacted for 20 minutes at the same temperature, and then for 20 minutes at −25° C. The reaction mixture was again cooled to −78° C., and 40 ml of a THF solution of 3.85 g (17 mmoles) of N-anisylcinnamylideneimine. After the addition, the temperature was gradually raised, and the mixture was reacted at room temperature for one day. The reaction mixture was poured into a 0.1M phosphate buffer (pH 5.5). The aqueous layer was adjusted to pH 4.0 with dilute hydrochloric acid, and then extracted with ethyl acetate. The ethyl acetate layer was washed with a saturated aqueous solution of sodium chloride and then dried over anhydrous sodium sulfate.

The organic layer was filtered and concentrated under reduced pressure. The residue was dissolved in a small amount of methylene chloride and adsorbed on a column packed with 150 g of silica gel. The column was diluted with benzene/ethyl acetate (10/1), (5/1) and (3/1) in this order. Those fractions in the eluates which showed a UV absorption at an Rf of 0.33 and 0.26 in silica gel TLC developed with the same mixed solvent (3/1) were collected, and dried under reduced pressure to give 993 mg of a compound 1a showing an Rf value of 0.33, 1.58 g of a mixture of compounds 1b and 1c showing an Rf value of 0.26, and 1.7 g of a mixture of compounds 1a, 1b and 1c. (Yield 78%).

Physicochemical properties of compound 1a:

$[\alpha]_D^{21}$ +157.7°(c = 1.0, CHCl$_3$)
$\lambda_{max}^{CH_2Cl_2}$ nm(ε): 257(35300)
$\nu_{max}^{CHCl_3}$ cm$^{-1}$: 1730(β-lactam)

NMR(CDCl$_3$)
δ:
 1.30(3H, d, J=7.0 Hz, C$\underline{H}$$_3$—CH)
 2.78(1H, br, OH)
 3.44(1H, t, J=6.0 Hz, H-3)
 3.79(3H, s, OMe)
 4.20(1H, m, C$\underline{H}$—CH$_3$)
 4.70(1H, dd, J=6.0 & 9.0 Hz, H-4)
 6.51(1H, dd, J=16.5 & 9.0 Hz,

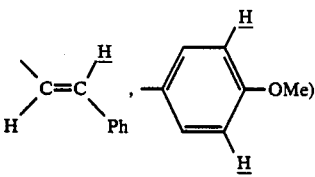

6.75-7.0(3H, m,

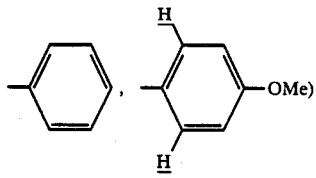

7.2-7.7(7H, m,

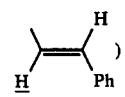

NMR Spectrum (CDCl$_3$) of compound Ib:
δ:
 1.40(3H, d, J=6.5 Hz, C$\underline{H}$$_3$—CH)
 2.75(1H, br, OH)
 3.11(1H, dd, J=3.0 & 6.0 Hz, H-3)
 3.71(3H, s, OMe)
 4.21(1H, m, C$\underline{H}$—CH$_3$)
 4.50(1H, dd, J=3.0 & 8.0 Hz, H-4)
 6.29(1H, dd, J-8.0 & 18.0 Hz,

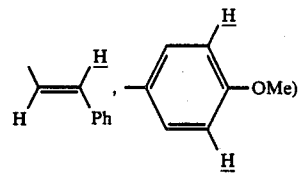

6.75-7.0(3H, m,

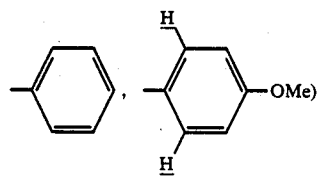

7.2-7.5(7H, m,

NMR Spectrum (CDCl$_3$) of compound Ic:
δ:
 1.37(3H, d, J=6.5 Hz, C$\underline{H}$$_3$—CH)
 4.72(1H, dd, J=2.5 & 8.0 Hz, H-4)
The other signals of the compound 1c were nearly the same as those of the compound 1b.

EXAMPLE 2

Production of (3R,4S)-3-[(R)-1-fluoroethyl]-1-(p-methoxy)phenyl-4-(2-phenyl)vinyl-2-azetidinone 2a:

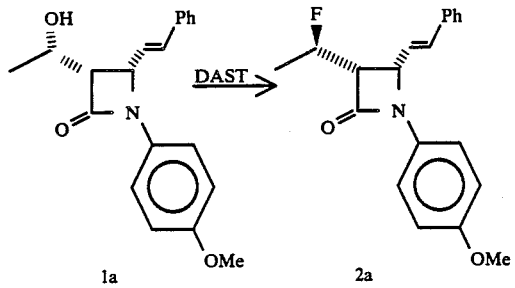

Five milliliters of anhydrous methylene chloride containing 250 microliters (2 mmoles) of diethylaminosulfur trifluoride (DAST) was cooled to −78° C., and a solution of 550 mg (1.7 millimoles) of (3S,4S)-3-[(S)-1-hydroxyethyl]-1-(p-methoxy)phenyl-4-(2-phenyl)vinyl-2-azetidinone 1a in anhydrous methylene chloride was gradually added dropwise. The mixture was reacted at the same temperature for 15 minutes. The raection mixture was poured into ice water, and methylene chloride and an aqueous solution of sodium hydrogen carbonate were added to perform extraction. The organic layer was washed with water and dried over anhydrous sodium sulfate. The dried product was concentrated under reduced pressure and adsorbed on a column packed with 25 g of silica gel. The column was eluted with benzene and benzene/ethyl acetate (50/1), (20/1), and (10/1). Those fractions in the eluates which showed an UV absorption at an Rf value of 0.25 in silica gel TLC developed with benzene/ethyl acetate (10/1) were collected and dried under reduced pressure to give 401 mg (yield 73%) of the desired compound 2a.

Physicochemical properties of compound 2a:

$[\alpha]_D^{21}$ +168.2°(c = 1.0, CHCl$_3$)
$\lambda_{max}^{CH2Cl2}$ nm($\epsilon$): 257(35400)
$\nu_{max}^{CHCl3}$ cm$^{-1}$: 1740($\beta$-lactam CO)

NMR(CDCl$_3$)
$\delta$:

1.53(3H, dd, J=24.0 & 6.5 Hz, CH$_3$—CHF—)
3.60(1H, m, H-3)
3.73(3H, s, OMe)
4.63–5.45(2H, m, H-4, CH$_3$—C$\underline{H}$F—)
6.20–7.50(11H, m, HC=CH—, Ar. H)

EXAMPLE 3

Production of (3R,4R)-3-[(R)-1-fluoroethyl]-1-(p-methoxy)phenyl-4-(2-phenyl)vinyl-2-azetidinone 2b:

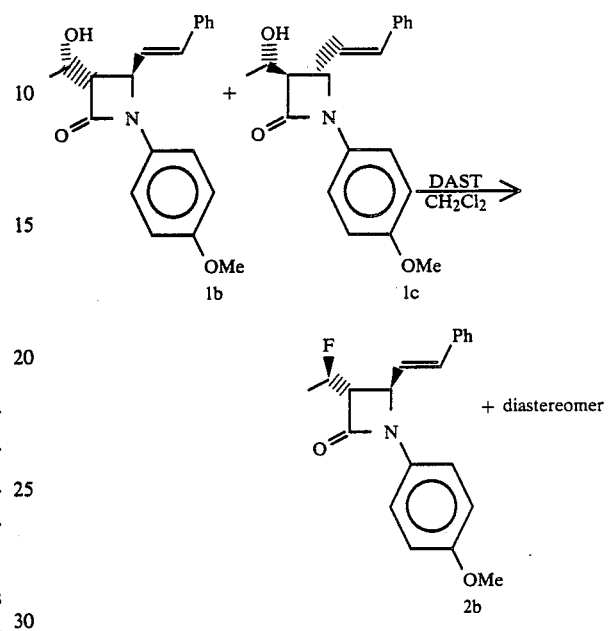

A solution of 562 microliters (4.61 mmoles) of dimethylaminosulfur trifluoride (DAST) in 3 ml of anhydrous methylene chloride was cooled to −65° C., and 6 ml of a methylene chloride solution of 745 mg (2.3 mmoles) of a mixture of (3S,4R) and (3R,4S)-3-[(S)-1-hydroxyethyl]-1-(p-methoxy)phenyl-4-(2-phenyl)vinyl-2-azetidinones 1b and 1c (3.5:1) was added dropwise over 15 minutes. The reaction solution was stirred for 2 hours at −65° to −30° C. and then for 15 hours at room temperature. The reaction mixture was poured into ice water-methylene chloride and then sodium hydrogen chloride was added. The mixture was allowed to separate into layers. The methylene chloride layer was washed with water and then dried over anhydrous sodium sulfate.

The solvent was evaporated, and the resulting syrup was adsorbed on a column packed with 30 g of silica gel. The column was eluted with benzene and benzene/ethyl acetate (50/1), (30/1), (20/1) and (1/1). Those fractions in the eluates which showed an UV absorption at an Rf value of 0.53 in silica gel TLC developed with benzene/ethyl acetate (10/1) were collected and dried under reduced pressure to give 755 mg of a mixture of compounds 2b and 2c. The mixture was dissolvd in a small amount of benzene, and n-hexane was slowly added to crystallize it. The crystals were collected by filtration and washed with n-hexane to give 457 mg (yield 61%) of compound 2b. Physicochemical properties of compound 2b:

Melting point: 117.0°–118.5° C.

$[\alpha]_D^{21}$ −135.5°(C = 1.0, CHCl$_3$)
$\lambda_{max}^{CH2Cl2}$ nm($\epsilon$): 256.6(35100)
$\nu_{max}^{CHCl3}$ cm$^{-1}$: 1740($\beta$-lactam CO)

NMR (CDCl$_3$)
$\delta$:

1.50(3H, dd, J=24.0 & 6.5 Hz, CH₃—F—)
3.23(1H, ddd, J=21.0 & 6.5 & 2.6 Hz, H-3)
3.76(3H, s, OMe)
4.67(1H, dd, J=8.0 & 2.5 Hz, H-4)
5.07(1H, d quint, J=49.0 & 6.5 Hz, CH₃—CHF—)
6.28(1H, dd, J=8.0 & 17.0 Hz,

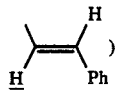
)

6.72-7.53(10H, m,

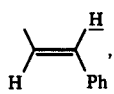
,

Ar H)

EXAMPLE 4-1

Synthesis of (3R,4S)-3-[(R)-1-fluoroethyl]-4-formyl-1-(p-methoxy)-phenyl-2-azetidinone 3b:

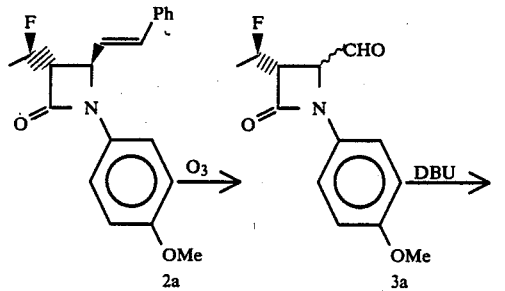

298 mg (0.916 mmole) of (3R,4S)-3-[(R)-1-fluoroethyl]-1-(p-methoxy)phenyl-4-(2-phenyl)vinyl-2-azetidinone 2a was dissolved in 20 ml of methanol-methylene chloride (1/1), and ozone was passed through the solution at −70° C. for 20 minutes. Then, 0.67 ml of dimethyl sulfide was added, and the mixture was reacted at room temperature for 16 hours. The reaction mixture was concentrated under reduced pressure, and the residue was dissolved in 5 ml of methylene chloride. Then, 20 microliters of 1,8-diazabicyclo[5.4.0]-7-undecene (DBU) was added, and the mixture was reacted at room temperature for 3 hours. The reaction mixture was adsorbed on a column packed with 15 g of silica gel. The column was eluted with benzene/ethyl acetate (10/1) and (5/1). Those fractions in the eluates which showed an UV absorption at an Rf value of 0.18 by silica gel TLC developed with benzene/ethyl acetate (3/1) were collected and concentrated under reduced pressure to give 91 mg (yield 40%) of the desired compound 3b. Physicochemical properties of compound 3b:

$[\alpha]_D^{21}$ −134.2°(c = 1.175, CHCl₃)
$\lambda_{max}^{CH_2Cl_2}$ nm(ε): 258(16100)

$\nu_{max}^{CHCl_3}$ cm⁻¹: 1750(β-lactam CO)

1730(aldehyde CO)

NMR(CDCl₃)
δ:
1.50(3H, dd, J=24.0 & 6.0 Hz) CH₃—CHF—)
3.42(1H, ddd, J=22.5 & 5.5 & 3.0 Hz, H-3)
3.78(3H, s, OMe)
4.50(1H, t, J=3.0 Hz, H-4)
5.07(1H, d quint, J=48.5 & 6.0 Hz, CH₃—CHF—)
6.88(2H, d, J=9.0 Hz,

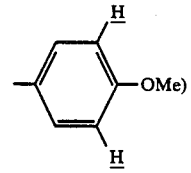
)

7.28(2H, d, J=9.0 Hz,

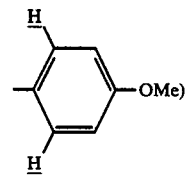
)

9.83(1H, d, J=3.0 Hz, —CHO)

EXAMPLE 4-2

Synthesis of compound 3b from compound 2b:

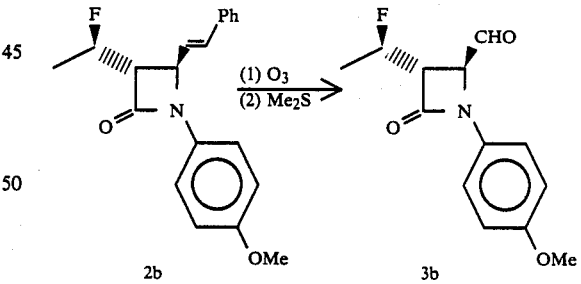

224 mg (0.69 mmoles) of (3R,4R)-3-[(R)-1-fluoroethyl]-1-(p-methoxy)phenyl-4-(2-phenyl)vinyl-2-azetidinone 2b was dissolved in 14 ml of methanol/methylene chloride (1/1), and while the solution was cooled at −70° C., ozone was blown into it for 10 minutes. Nitrogen gas was blown into the solution to remove the excess of ozone, and 0.51 ml (6.94 mmoles) of dimethyl sulfide was added at −70° C. The mixture was stirred at room temperatature for 14 hours. The mixture was further heated at 40° C. for 5 hours. The reaction mixture was then concentrated under reduced pressure to give a syrup. The syrup was chromatographed on a column of silica gel (12 g), and worked up as in Example 4-1 to give 126 mg (yield 73%) of the desired compound 3b as a colorless syrup.

EXAMPLE 5

Synthesis of (3R,4S)-4-carboxy-3-[(R)-1-fluoroethyl]-1-(p-methoxy)-phenyl-2-azetidinone 4b:

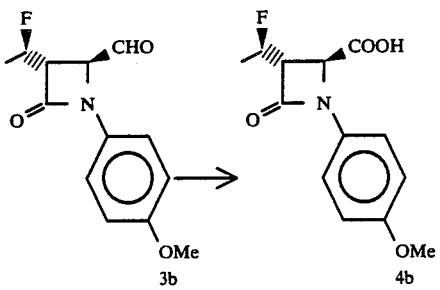

112 mg (0.4462 mmole) of (3R,4S)-3-[(R)-1-fluoroethyl]-4-formyl-1-(p-methoxy)phenyl-2-azetidinone 3b was dissolved in 3 ml of acetone. Under ice cooling, 0.19 ml (0.49 mmole) of Jones reagent was added. The mixture was reacted at the above temperature for 2 hours. 0.2 ml of isopropanol was added, and the mixture was stirred for 10 minutes. The reaction mixture was poured into 30 ml of ethyl acetate, and washed with a saturated aqueous solution of sodium chloride and water. The organic layer was dried over anhydrous sodium sulfate, filtered, and concentrated under reduced pressure. The concentrate was adsorbed on a column of silica gel (17 g), and the column was eluted with bezene/acetone (5/11) and (1/1), acetone, and methanol in this order. Those fractions in the eluates which showed an UV absorption at an Rf value of 0.14 in silica gel TLC developed with ethyl acetate/methanol (3/1) were collected and concentrateed under reduced pressure. The residue was dissolved in acetone, and filtered by a No. 4 glass filter. The filtrate was dried under reduced pressure to give 76 mg (yield 64%) of the desired compound 4b.

Physicochemical properties of compound 4b:

$[\alpha]_D^{21}$: −40.8°(c = 1, MeOH)
$\lambda_{max}^{MeOH}$ nm($\epsilon$): 257.5(22600)
$\nu_{max}^{KBr}$ cm$^{-1}$: 1745($\beta$-lactam CO)

NMR(CD$_3$COCD$_3$)
$\delta$:

1.40(3H, dd, J=6.5 & 24.5 Hz, C$\underline{H}_3$—CHF—)
3.53(1H, m, H-3)
3.77(3H, s, OMe)
4.43(1H, d, J=2.0 Hz, H-4)
5.04(1H, m, CH3—C$\underline{H}$F—)
6.88(2H, d, J=9.0 Hz,

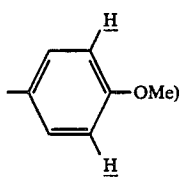

7.41(2H, d, J=9.0 Hz,

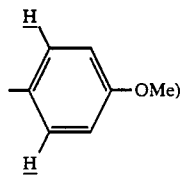

EXAMPLE 6

Production of (3R,4R) and (3R,4S)-4-acetroxy-3-[(R)-1-fluoroethyl]-1-(p-methoxy)phenyl-2-azetidinones 5b and 5a:

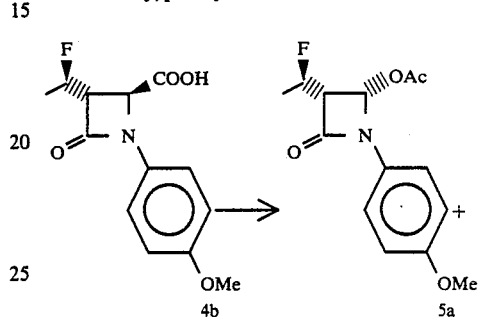

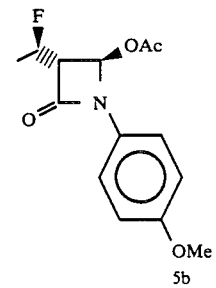

A mixture of 65 mg (0.24 mmole) of (3R,4S)-4-carboxy-3-[(R)-fluoroethyl]-1-(p-methoxy)phenyl-2-azetidinone, 216 mg (0.49 mmole) of lead tetraacetate, 0.2 ml of acetic acid and 0.6 ml of dimethylformamide was reacted at 65° C. for 15 minutes. The reaction mixture was poured into ethyl acetate, washed with a saturated aqueous solution of sodium chloride, and dried over anhydrous sodium sulfate. The solvent was evaporated, and the residue was dissolved in benzene and adsorbed on a column of silica gel (7 g). The column was eluted with benzene and benzene/ethyl acetate (50/10), (40/1) and (20/1). Those fractions in the eluates which showed an UV absorption at an Rf value of 0.75 and 0.57 in silica gel TLC developed with benzene/ethyl acetate (3/1) were collected and concentrated under reduced pressure to give 7 mg and 3 mg of the desired compounds 5a and 5b (total yield 73%). The compuonds 5a and 5b were crystallized from benzene/n-hexane.

Physicochemical properties of compound 5a:
Melting point: 156°-160° C.

$[\alpha]_D^{22}$: +42.7°(c = 0.62, CHCl$_3$)
$\lambda_{max}^{CH_2Cl_2}$ nm($\epsilon$): 255(21000)
$\nu_{max}^{CHCl_3}$ cm$^{-1}$: 1760($\beta$-lactam, ester CO)

NMR(CDCl$_3$)
$\delta$:

1.60(3H, dd, J=24.0 and 6.0 Hz, C$\underline{H}_3$—CHF)

2.17(3H, s, OAc)
3.68(1H, m, H-3)
3.70(3H, s, OMe)
5.17(1H, m, CH₃—C<u>H</u>F)
6.83(1H, d, J=6.0 Hz, H-4)
6.90(2H, d, J=9.0 Hz,

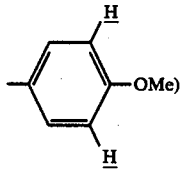

7.37(2H, d, J=9.0 Hz,

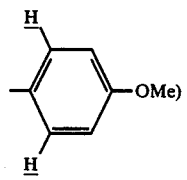

Physicochemical properties of compound 5b:
Melting point: 121°-123.5° C.

$[\alpha]_D^{22}$: -51.4°(c = 1.013, CHCl₃)
$\lambda_{max}^{CH2Cl2}$ nm($\epsilon$): 254(18400)
$\nu_{max}^{CHCl3}$ cm⁻¹: 1760(β-lactam, ester CO)

NMR(CDCl₃)
δ:
1.55(3H, d, J=24.0 & 6.5 Hz, C<u>H</u>₃—CHF)
2.10(3H, s, OAc)
3.40(1H, ddd, J=1.5 & 5.0 & 24.5 Hz, H-3)
3.79(3H, s, OMe)
5.07(1H, ddq, H=48.0 & 5.0 & 6.5 Hz, CH₃—C<u>H</u>F—)
6.62(1H, d, J=1.5 Hz, H-4)
6.90(2H, d, J=9.0 Hz,

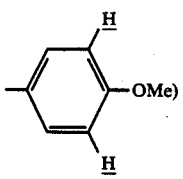

7.36(2H, d, J=9.0 Hz,

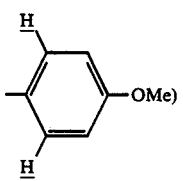

EXAMPLE 7

Production of (3R,4R)-4-acetoxy-3-[(R)-1-fluoroethyl]-2-azetidinone 6b:

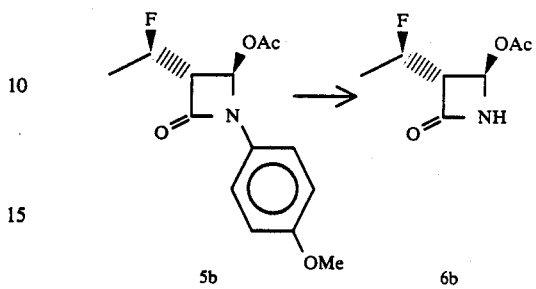

Thirty milligrams (0.11 mmole) of (3R,4R)-4-acetoxy-3-[(R)-fluoroethyl]-1-(p-methoxy)phenyl-2-azetidinone 5b was dissolved in 1.5 ml of acetonitrile, and the solution was cooled with ice. Then, 1.5 ml of an aqueous solution of 175.5 mg (0.32 mmole) of ceric ammonium nitrate was gradually added dropwise.

The reaction was carried out for 25 minutes at the above temperature. The reaction solution was poured into 50 ml of ethyl acetate, and washed with a 5% aqueous solution of sodium hydrogen carbonate. The washing was again extracted with ethyl acetate. The organic layers were combined, and washed once with a 10% aqueous solution of sodium thiosulfate, a 5% aqueous solution of sodium hydrogen carbonate and a saturated aqueous solution of sodium chloride.

The washed organic layer was dried over anhydrous sodium sulfate, and concentrated under reduced pressure to give 15 mg (yield 81%) of the desired compound 6b.

The compound 6b was crystallized from benzene/n-hexane.
Melting point: 98.5°-102° C.

$[\alpha]_D^{22}$: +116.8(c = 1.0, CHCl₃)
$\nu_{max}^{CHCl3}$ cm⁻¹: 1780(β-lactam CO)
1745(ester CO)

NMR(CDCl₃)
δ:
1.50(3H, dd, J=6.5 & 24.0 Hz, C<u>H</u>₃—CHF)
2.13(3H, s, COCH₃)
3.40(1H, ddd, J=1.5 & 5.5 & 24.0 Hz, H-3)
5.00(1H, dqiunt, J=48.0 & 6.5 Hz, CH₃—C<u>H</u>F—)
5.90(1H, d, J=1.5 Hz, H-4)
6.85(1H, br, NH)

EXAMPLE 8

Synthesis of p-nitrobenzyl 4-{(3R,4R)-3-[(R)-1-fluoroethyl]-2-oxoazetidin-4-yl}-2-diazo-3-ozobutyrate 7b:

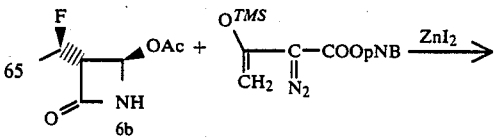

-continued

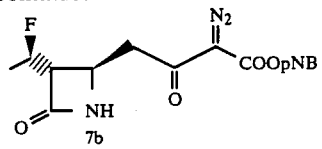

Twenty milligrams (0.11 mmole) of (3R,4R)-4-acetoxy-3-[(R)-fluoroethyl]-2-azetidinone 6b was dissolved in 1 ml of methylene chloride. The solution was cooled with ice and 36 mg (0.11 mmole) of zinc iodide was added. One milliliter of a methylene chloride solution of 96 mg (0.29 mmole) of p-nitrobenzyl 2-diazo-3-trimethylsilyloxy-3-butenoate was slowly added dropwise to the mixture over the course of 13 minuites.

The reaction mixture was stirred for 20 minutes at 0° C. and then for 2 hours at room temperatures. After the reaction, the reaction mixture was diluted with ethyl acetate, washed successively with a 5% aqueous solution of sodium hydrogen carbonate, water and a saturated aqueous solution of sodium chloride, and dried over anhydrous sodium sulfate.

The solvent was evaporated, and the residue was dissolved in a small amount of methylene chloride and adsorbed on a column of silica gel (6 g). The column was eluted with benzene/acetone (10/1), (8/1) and (5/1) in this order. Those fractions in the eluates which showed an UV absorption at an Rf of 0.36 in TLC developed with benzene/acetone (3/1) were collected and dried under reduced pressure to give 27 mg (yield 62%) of the desired compound 7b.

Physicochemical properties of compound 7b:
Melting point: 90°-92° C.

$[\alpha]_D^{22}$: +41.8°(C 1.25, methanol)

$\nu_{max}^{CHCl_3}$ cm$^{-1}$: 2140(diazo)

1760(β-lactam CO)
   1710(ketone CO)
   1520, 1345(nitro)

NMR(CDCl$_3$)
δ:
1.44(3H, dd, J=24.0 and 6.5 Hz, C$\underline{H}_3$—CHF—)
2.8-3.2(1H, m, H-3)
3.02(1H, dd, J=18.0 and 9.0 Hz,

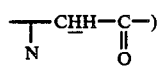

3.67(1H, dd, J=18.0 and 4.5 Hz,

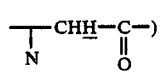

4.02(1H, ddd, J=9.0, 4.5 and 2.3 Hz, H-4)
4.93(1H, dqunit, J=48.0 and 6.5 Hz, CH$_3$C$\underline{H}$—F—)
5.38(2H, s, benzyl)
6.30(1H, br, NH)
7.56(2H, d, J=9.0 Hz, Ar)
8.28(2H, d, J=9.0 Hz, Ar)

EXAMPLE 9

Production of (3R,4S)-4-acetoxy-3-[(R)-1-fluoroethyl]-2-azetidinone 6a:

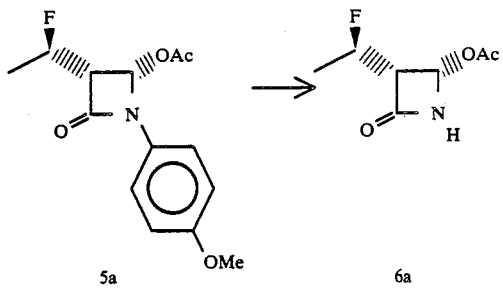

27 mg (0.096 mmole) of (3R,4S)-4-acetoxy-3-[(R)-1-fluoroethyl]-1-(p-methoxy)phenyl-2-azetidinone 5a was dissolved in 1.0 ml of acetonitrile, and the solution was cooled with ice. Then, 1.0 ml of an aqueous solution of 132 mg (0.24 mmole) of ceric ammonium nitrate was slowly added dropwise.

At the above temperature, the mixture was reacted for 30 minutes, and the reaction mixture was poured into ethyl acetate, and washed with a 5% aqueous solution of sodium hydrogen carbonate. The aqueous layer was again extracted with ethyl acetate. The organic layers were combined, and washed successively with a 10% aqueous solution of sodium thiosulfate, a 5% aqueous solution of sodium hydrogen carbonate and a saturated aqueous solution of sodium chloride.

The washed product was dried over anhydrous sodium sulfate, and then the solvent was evaporated to give 15 mg (yield 89%) of the desired compound 6a.

$\nu_{max}^{CHCl_3}$ cm$^{-1}$: 3390(NH)

1780(β-lactam CO)
   1735(ester CO)

NMR(CDCl$_3$)
δ:
1.55(3H, dd, J=6.0 and 24.0 Hz, C$\underline{H}_3$CHF—)
2.17(3H, s, COCH$_3$)
3.58(1H, dddd, J$_3$NH=2.0, J$_{3,4}$=4.5, J$_3$,CHF=9.3, J$_3$F=13.8 Hz, H-3)
5.13(1H, ddq, J=6.0, 9.3 and 48.0 Hz, CH3C$\underline{H}$F—)
6.02(1H, d, J=4.5 Hz, H-4)
6.80(1H, br, NH)

EXAMPLE 10

Synthesis of p-nitrobenzyl 4-{(3R,4R)-3-[(R)-1-fluoroethyl]-2-oxoazetidin-4-yl}-2-diazo-3-oxobutyrate 7b:

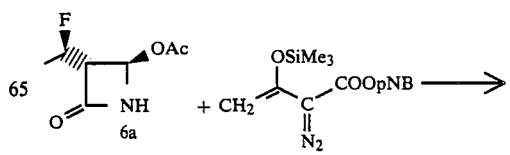

-continued

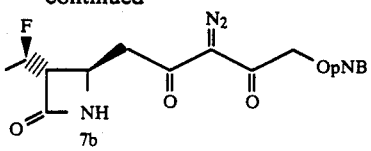
7b

Fifteen milligrams (0.086 mmole) of (3R,4S)-4-acetoxy-3-[(R)-fluoroethyl]-2-azetidinone 6a was dissolved in 1 ml of methylene chloride. The solution was cooled with ice, and 28 mg (0.087 mmole) of zinc iodide was added. A methylene chloride solution (0.5 ml) of 72 mg (0.21 mmole) of p-nitrobenzyl 2-diazo-3-(trimethylsilyl)oxy-3-butenoate was added dropwise slowly over 10 minutes.

The reaction mixture was stirred for 10 minutes at 0° C., and then for 2 hours at room temperature. The reaction mixture was diluted with ethyl acetate, washed successively with a 5% aqueous solution of sodium hydrogen carbonate, water and a saturated aqueous solution of sodium chloride, and dried over anhydrous sodium sulfate. The residue was purified by TLC (developer: benzene/acetone=3/1) to give 13.7 mg (yield 42%) of the desired compound 7b.

The physicochemical propretises of the resulting compound 7b completely agreed with those of the product obtained in Example 8.

EXAMPLE 11

Production of (3R,4S)- and (3R,4R)-4-(diethoxy)-methyl-3-[(S)-1-hydroxyethyl]-1-(p-methoxy)phenyl-2-azetidinones 11a and 11b:

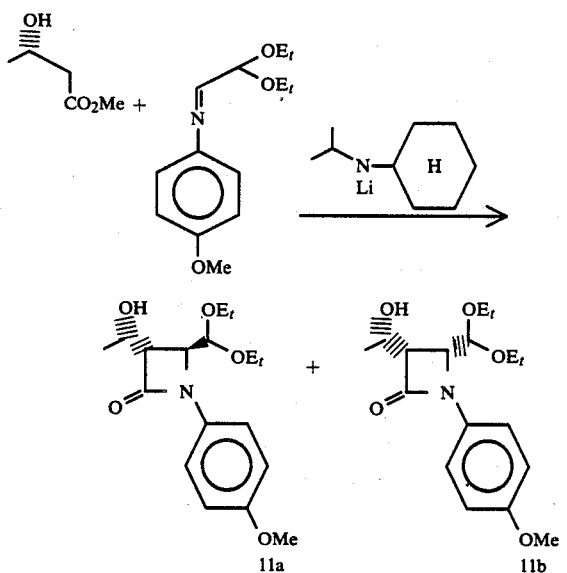

An anhydrous tetrahydrofuran solution (4 ml) of 0.691 ml (4.2 mmoles) of N-isopropylcyclohexylamine was cooled to −45° C., and 2.62 ml (4.2 mmoles) of a 1.6M n-hexane solution of n-butyllithium was added dropwise to the cooled solution. The reaction mixture was stirred at −45° C. for 1 hour.

A tetrahydrofuran solution (1.5 ml) of 236 mg (2.0 mmoles) of methyl(S)-beta-hydroxybutyrate was slowly added dropwise to the reaction mixture. The mixture was stirred at −45° C. for 2 hours, and an N,N-dimethylformamide solution (5 ml) of 522 mg (2.2 mmoles) of N-anisyl-(2,2-diethoxyethyl)mine was slowly added dropwise over the course of about 15 minutes.

After the addition, the reaction mixture was gradually heated to room temperature from −45° C., and stirred overnight.

The reaction mixture was cooled with ice, and a saturated aqueous solution of ammonium chloride and ethn ethyl acetate were added. The mixture was stirred for a while. After separation, the aqueous layer was extracted with ethyl acetate. The organic layers were combined, washed successively with a cold 0.5N aqueous solution of hydrochloric acid, a saturated aqueous solution of sodium hydrogen carbonate and then a saturated aqueous solution of sodium chloride, dried over anhydrous sodium sulfate. The solvent was evaporated. The residue was adsorbed on a column of silica gel (25 g). The column was eluted stepwise with benzene/ethyl cetate (10/1), (5/1), (3/1) and (1/1). Those fractions in the eluates which showed an UV absorption at an RF of 0.39 and 0.29 in TLC developed with benzene/ethyl acetate (2/1) and fractions which showed an UV absorption only at an Rf of 0.29 were collected and concentrated to give 51.8 mg (8.0%) of a mixture of comlpoundsd 11a and 11b (11a:11b=about 1:4) and 271.8 mg (42.0%) of compound 11a each as a colorless syrup.

Physicochemical properties of compound 11a:

$[\alpha]_D^{24}$: −36.8°(C 1.02, $CH_2Cl_2$)
$\lambda_{max}^{CH_2Cl_2}$ nm($\epsilon$): 258.0(19500)
$\nu_{max}^{CHCl_3}$ cm$^{-1}$: 3400, 1730

$^1$H NMR($CDCl_3$)

δ:

1.17(3H, t, J=7.5 Hz, $OCH_2\underline{C}H_3$)
1.33(3H, t, J=7.5 Hz, $OCH_2\underline{C}H_3$)
1.47(3H, d, J=6.8 Hz, $\underline{C}H_3CH(OH)$—)
2.55(1H, b, OH)
3.34(1H, dd, J=2.4 and 6.0 Hz, H-3)
3.35–3.95(4H, m, 2×$O\underline{C}H_2CH_3$)
3.85(3H, S, OMe)
4.06(1H, dd, J=2.4 and 4.5 Hz, H-4)
4.0–4.4(1H, m, $CH_3\underline{C}H(OH)$—)
4.75(1H, d, J=4.5 Hz, —$\underline{C}H(OE_t)_2$)
6.95(2H, d, J=9 Hz, phenyl)
7.52(2H, d, J=9 Hz, phenyl)

Physicochemical properteis of compound 11b:

$[\alpha]_D^{23}$: +73.4°(C 0.7, $CH_2Cl_2$)
$\lambda_{max}^{CH_2Cl_2}$ nm($\epsilon$): 257.5(16500)
$\nu_{max}^{CHCl_3}$ cm$^{-1}$: 3410, 1735

$^1$H NMR($CDCl_3$)

δ:

1.16(6H, t, J=7.5 Hz, 2×$OCH_2\underline{C}H_3$)
1.22(3H, d, J=6.8 Hz, $\underline{C}H_3CH(OH)$—)
3.2(1H, b, OH)
3.3–4.0(5H, m, H-3 and 2×$O\underline{C}H_2CH_3$)
3.84(3H, S, OMe)
4.26(1H, t, J=6.0 Hz, H-4)
4.2–4.6(1H, m, $CH_3\underline{C}H(OH)$—)
5.12(1H, d, J=6.0 Hz, —$\underline{C}H(OE_t)_2$)
6.92(2H, d, J=9.5 Hz, phenyl)
7.55(2H, d, J=9.5 Hz, phenyl)

EXAMPLE 12

Production of (3R,4R)-4-(diethoxy)methyl-3-[(R)-1-fluoroethyl]-1-(p-methoxy)phenyl-2-azetidinone (12)

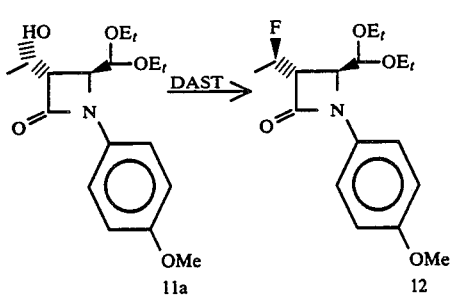

A methylene chloride solution (1.5 ml) of 114 microliters (0.934 mmole) of diethylaminosulfur trifluoride was cooled to $-70°$ C., and with stirring, a methylene chloride solution (2.0 ml) of 151 mg (0.467 mmole) of (3R,4S)-4-(diethoxy)methyl-3-[(S)-1-hydroxyethyl]-1-(p-methoxy)phenyl-2-azetidine (11a) was slowly added dropwise to the cooled solution. The reaction mixture was stirred overnight while it was gradually heated to room temperature from $-79°$ C.

The reaction mixture was poured into a cold saturated aqueous solution of sodium hydrogen carbonate, and then methylene chloride was added to separate it into layers. The aqueous layers was extracted with methylene chloride. The organic layers were combined, washed with a saturated aqueous solution of sodium chloride, and driec over sodium sulfate.

The solvent was evaporated, and the resultilng syrup was chromatographed over a column of silica gel (13 g). The column was eluted stepwise with benzene/ethyl acetate (20/1) and (10/1). Fractions in the eluates which showed an UV absorption at an Rf of 0.40 in TLC developed with benzene/ethyl acetate (7/1) were collected and concentrated under reduced pressure to give 92 mg (61%) of the capitoned compound as a colorless syrup.

$[\alpha]_D^{22}$: $-56.6°$(C 0.92, CH$_2$Cl$_2$)
$\lambda_{max}^{CH_2Cl_2}$ nm($\epsilon$): 258.2(19700)
$\nu_{max}^{CHCl_3}$ cm$^{-1}$: 1740

$^1$H NMR(CDCl$_3$)
δ:
1.14(3H, t, J=7.5 Hz, OCH$_2$CH$_3$)
1.20(3H, t, J=7.5 Hz, OCH$_2$CH$_3$)
1.48(3H, dd, J=6.5 and 24.5 Hz, CH$_3$CHF—)
3.26-4.00(5H, m, H-3 and 2×OCH$_2$CH$_3$)
3.83(3H, S, OMe)
4.25(1H, dd, J=2.1 and 3.3 Hz, H-4)
4.80(1H, d, J=3.3 Hz, CH(OE$_t$)$_2$)
4.65-5.60(1H, m, CH$_3$CHF—)
6.92(2H, d, J=9 Hz, phenyl)
7.52(2H, d, J=9 Hz, phenyl)

EXAMPLE 13

Production of (3R,4S)-3-[(R)-1-fluoroethyl]-4-formyl-1-(p-methoxy)phenyl-2-azetidinone (13):

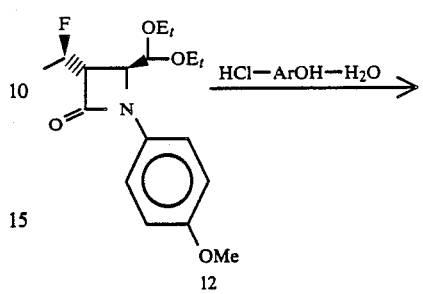

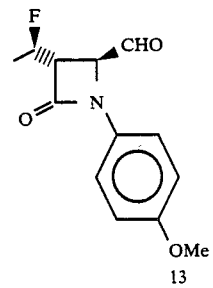

92 mg (0.28 mmole) of (3R,4S)-4-(diethoxy)methyl-3[(R)-1-fluoroethyl]-1-(p-methoxy)phenyl-2-azetidinone (12) was dissolved in acetic acid (1.6 ml) and water (0.4 ml), and a 1N aqueous solution of hydrochloric acid (0.6 ml) was added. The mixture was heated at 55° to 60° C. for 10 hours with stirring.

The reaction mixture was diluted with ethyl acetate, and while being stirred at 0° C., neutralized with a saturated aquoeus solution of sodium hydrogen carbonate. After separation of the mixture into layers, the aqueous layer was extracted with ethyl acetate. The organic layers were combined, washed with a saturated aqueous solution of sodium chloride, and dried over anhydrous sodium sulfate.

The solvent was evaporated, the the resulting syrup was adsorbed on a column of silica gel (5 g). The column was diluted with benzene/ethyl acetate (4/1). Fractions in the eluates which showed an UV absorption at an Rf of 0.2 in TLC developed with enzene/ethyl cetate (2/1) wre collected and concentrated under reduced pressure to give 64.0 mg (90%) of the captioned compound as a colorless syrup.

$[\alpha]_D^{21}$: $-134.2°$(C 1.175, CHCl$_3$)
$\lambda_{max}^{CH_2Cl_2}$ nm($\epsilon$): 258.0(16100)
$\nu_{max}^{CHCl_3}$ cm$^{-1}$: 1750, 1730

$^1$H NMR(CDCl$_3$)
δ:
1.50(3H, dd, J=6.0 and 24.0 Hz, CH$_3$CF—)
3.42(1H, ddd, J=6.0 and 22.5 Hz, H-3)
3.78(3H, S, OMe)
4.50(1H, t, J=3.0 Hz, H-4)
5.07(1H, dquint. J=6.0 and 48.5 Hz, CH$_3$CHF—)
6.88(2H, d, J=9 Hz, phenyl)
7.28(2H, d, J=9 Hz, phenyl)
9.83(1H, d, J=3.0 Hz, —CHO)

EXAMPLE 14

Production of (3R,4S)-4-carboxy-3-[(R)-1-fluoroethyl]-1-(p-methoxy)-phenyl-2-azetidinone (14):

112 mg (0.446 mmole) of (3R,4S)-3-[(R)-1-fluoroethyl]-4-formyl-1-(P-methoxy)phenyl-2-azetidinone (13) was dissolved in acetone (3 ml), and with stirring at 0° C., 0.19 ml (0.49 mmole) of Jones reagent was added dropwise. The mixture was stirred at 0° C. for 2 hours.

To the reaction mixture was added 0.2 ml of 2-propanol, and the mixture was stirred for 10 minutes and then poured into ethyl acetate. It was washed successively with water and a saturated aqueous solution of sodium chloride. Acidic components were extracted from the organic layer using a cold dilute aqueous solution of sodium hydrogen carbonate. After separation into layers, the aqueous layer was adjusted to pH 2-3 with a 1N aqueous solution of hydrochloric acid, and extracted twice with ethyl acetate.

The organic layers were combined, washed with a saturated aqueous solution of sodium chloride and dried over anhydrous sodium sulfate. The solvent was evaporated to give 76 mg (yield 76 mg) of the captioned compound as an amorphous solid.

$[\alpha]_D^{23}$: $-79.4°$ (C 0.97, MeOH)

$\lambda_{max}^{MeOH}$ nm($\epsilon$): 256.5(20800)

$\nu_{max}^{KBR}$ cm$^{-1}$: 3080, 1750, 1720

$^1$H NMR(acetone-d$_6$)
$\delta$:
1.55(3H, dd, J=6.5 and 24.3 Hz, CH$_3$CF—)
3.73(1H, ddd, J=6.0, 5.3 and 25.5 Hz, H-3)
3.87(3H, S, OMe)
4.75(1H, d, J=3.0 Hz, H-4)
5.25(1H, dqd, J=5.3, 6.5 and 49.0 Hz, CH$_3$C$\underline{H}$F—)
7.03(2H, d, J=9 Hz, phenyl)
7.52(2H, d, J=9 Hz, phenyl)
7.6–8.0(1H, b, COOH)

What we claim is:

1. An azetidinone derivative of the formula wherein R$_1$ represents a formyl group, a carboxyl group, or a group of the formula in which R$_2$ and R$_3$ each represent a lower alkyl group or together represent a lower alkylene group, and Z represents a hydrogen atom or an amino-protecting group.

2. The azetidinone derivative of claim 1 wherein the amino-protecting group is selected from tri-(lower alkyl)silyl groups, aralkyl groups and substituted or unsubstituted phenyl groups.

3. The azetidinone derivative of claim 1 which is (3R,4S)-3-[(R)-1-fluoroethyl]-1-(p-methoxy)phenyl-4-(2-phenyl)vinyl-2-azetidinone.

4. The azetidinone derivative of claim 1 which is (3R,4S)-4-carboxy-3-[(R)-1-fluoroethyl]-1-(p-methoxy)-phenyl-2-azetidinone.

5. The azetidinone derivative of claim 1 which is (3R,4R)-4-(diethoxy)methyl-3[(R)-1-fluoroethyl]-1-(p-methoxy)phenyl-2-azetidinone.

* * * * *